(12) United States Patent
Bellón Caneiro et al.

(10) Patent No.: US 9,119,698 B2
(45) Date of Patent: Sep. 1, 2015

(54) WALL PROSTHESIS THAT CAN BE IMPLANTED IN THE CENTER OF A WOUND TO REINFORCE ABDOMINAL WALL CLOSURE

(75) Inventors: Juan Manuel Bellón Caneiro, Madrid (ES); Pedro López Hervás, Madrid (ES); Julia Buján Varela, Madrid (ES)

(73) Assignees: Juan Manuel Bellon Caneiro, Madrid (ES); Pedro Lopez Hervas, Madrid (ES); Julia Bujan Varela, Madrid (ES)

( * ) Notice: Subject to any disclaimer, the term of this patent is extended or adjusted under 35 U.S.C. 154(b) by 2805 days.

(21) Appl. No.: 10/485,859

(22) PCT Filed: Jul. 31, 2002

(86) PCT No.: PCT/ES02/00384
§ 371 (c)(1),
(2), (4) Date: Oct. 8, 2004

(87) PCT Pub. No.: WO03/011181
PCT Pub. Date: Feb. 13, 2003

(65) Prior Publication Data
US 2005/0043818 A1 Feb. 24, 2005

(30) Foreign Application Priority Data
Aug. 3, 2001 (ES) .................................. 200101825

(51) Int. Cl.
*A61F 2/00* (2006.01)
*A61L 27/58* (2006.01)
*A61B 17/00* (2006.01)

(52) U.S. Cl.
CPC ..... *A61F 2/0063* (2013.01); *A61B 2017/00637* (2013.01); *A61L 27/58* (2013.01)

(58) Field of Classification Search
USPC ................. 623/23.72–23.74; 600/37; 606/215
See application file for complete search history.

(56) References Cited

U.S. PATENT DOCUMENTS 4,531,521 A * 7/1985 Haverstock .................. 606/215
4,769,038 A 9/1988 Bendavid et al.
(Continued)

FOREIGN PATENT DOCUMENTS

EP 0 362 113 4/1990
EP 0 474 887 3/1992
(Continued)

OTHER PUBLICATIONS

"Closure of mid-line laparotomy incisions with polydioxanone and nylon: The importance of suture technique", Israelsson, L.A., Jonsson, T., Br. Journal of Surgery, 1994, 81, 1606-1608.
(Continued)

*Primary Examiner* — David H Willse
(74) *Attorney, Agent, or Firm* — Wenderoth, Lind & Ponack, L.L.P.

(57) ABSTRACT

The invention relates to a prosthesis that can be implanted in the center of wall wound scarring. The inventive prosthesis, which is intended for use in abdominal surgery, is provided with a geometric shape in the form of sheets that converge in dihedral angles. The sheets or planes are made from a synthetic biotolerated material in porous form with large pores. One of the planes is inserted into the center of the scarring between the two aponeurotic surfaces to be joined. The other plane(s) of the prosthesis, which is perpendicular to the aforementioned plane, is arranged so as to overlap the aponeurotic edges of the edge of the section. The proliferation obtained around the prosthesis, in the scarring center and close thereto, provides stress resistance greater than that obtained in standard closures, thereby greatly reducing the risk of hernias caused by a badly healed wound.

58 Claims, 2 Drawing Sheets

(56) References Cited

U.S. PATENT DOCUMENTS

| | | | |
|---|---|---|---|
| 4,923,464 A | | 5/1990 | DiPisa, Jr. |
| 5,061,274 A | | 10/1991 | Kensey |
| 5,116,357 A | | 5/1992 | Eberbach |
| 5,192,302 A | | 3/1993 | Kensey et al. |
| 5,254,133 A | * | 10/1993 | Seid ............... 606/215 |
| 5,350,399 A | | 9/1994 | Erlebacher et al. |
| 5,356,432 A | * | 10/1994 | Rutkow et al. ............. 623/23.72 |
| 5,366,460 A | | 11/1994 | Eberbach |
| 5,370,650 A | | 12/1994 | Tovey et al. |
| 5,397,331 A | | 3/1995 | Himpens et al. |
| 5,531,759 A | | 7/1996 | Kensey et al. |
| 5,540,711 A | * | 7/1996 | Kieturakis et al. ............ 606/192 |
| 5,545,178 A | | 8/1996 | Kensey et al. |
| 5,634,944 A | * | 6/1997 | Magram .................... 623/15.12 |
| 5,697,978 A | | 12/1997 | Sgro |
| 5,725,577 A | * | 3/1998 | Saxon ........................ 623/23.72 |
| 5,743,917 A | | 4/1998 | Saxon |
| 6,066,777 A | * | 5/2000 | Benchetrit ................... 424/423 |
| 6,113,623 A | | 9/2000 | Sgro |
| 6,241,768 B1 | * | 6/2001 | Agarwal et al. ............ 623/11.11 |
| 6,383,201 B1 | * | 5/2002 | Dong ........................... 606/151 |
| 2001/0027347 A1 | | 10/2001 | Rousseau |

FOREIGN PATENT DOCUMENTS

| | | | | |
|---|---|---|---|---|
| FR | 2778554 | | 11/1999 | |
| GB | 1 217 944 | * | 1/1971 | .................... 606/215 |
| SU | 676285 | | 7/1979 | |
| WO | WO 90/14796 A1 | | 12/1990 | |
| WO | WO 96/40307 A1 | | 12/1996 | |
| WO | WO 99/39645 A1 | | 8/1999 | |
| WO | WO 99/56664 A1 | | 11/1999 | |
| WO | WO 00/42943 A1 | | 7/2000 | |

OTHER PUBLICATIONS

"A biomechanical study of suture pullout in linea alba", Campbell, J.A., Temple, W.J., Frank, C.E., Huchcroft, S.A., Surgery, Nov. 1989, vol. 106, No. 5.

"The Abdominal Linea Alba: Anatomo-Radiologic and Biomechanical study", Rath, A.M., Attali, P., Dumas, J.L., Goldlust, D., Zhang, J., Chevrel, J.P., surgical and medealogic anatomy (general of clinical anatomy) 1996, 18: 281-288.

Incisional hernia after mid-line laparotomy: A perspective study, Israelsson, L.A., Jonsson, T., European Journal of Surgery, 1996: 162: 125-129.

"Influence of Suture Material and Suture Technique on Collagen Fibril Diameters in Mid-Line Laparotomies", Hoer, J., Anurov, M., Titkova, S., Klinge, U., Tons, C., Ottinger, A., Schumpelick, V., European Surgical Research, 2000: 32: 359-367.

"Small tissue bites and wound strength: An experimental study", Cengiz, Y., Blonquist, P., Israelsson, L.A., Archives of Surgery, vol. 136, Mar., 2001.

"Suture Length to Wound Length Ratio and Healing of Mid-line Laparotomy Incisions", Israelsson, L.A., Jonsson, T., Br. Journal of Surgery, 1993, vol. 8, Oct. 1284-1286.

* cited by examiner

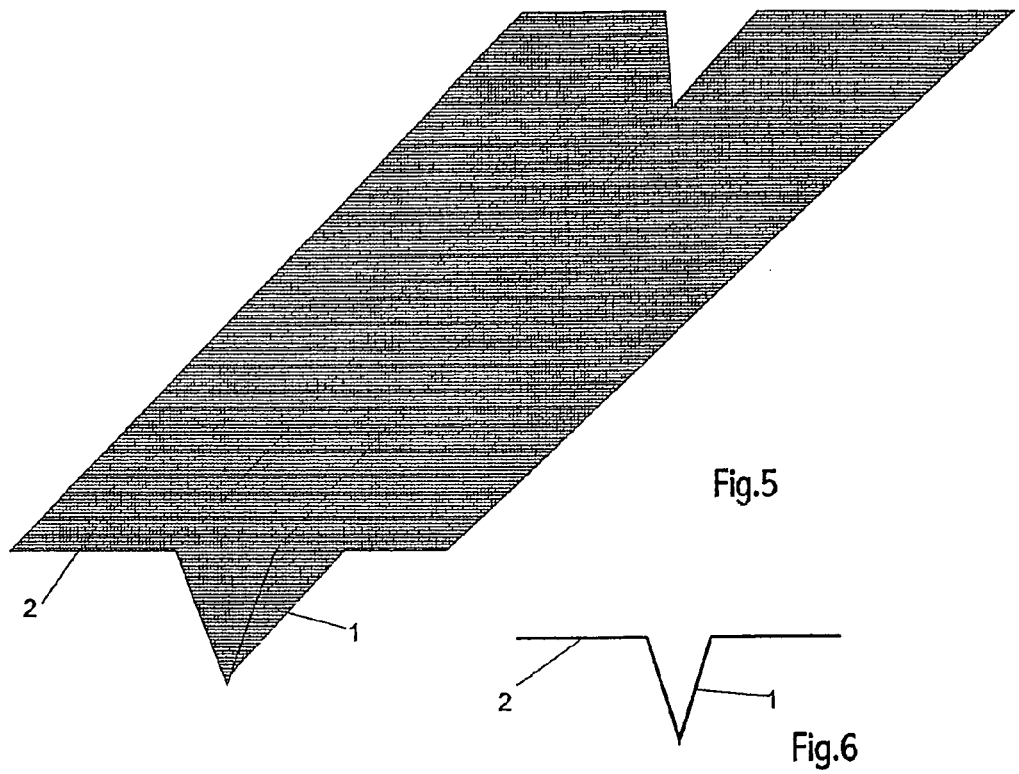
Fig.5
Fig.6
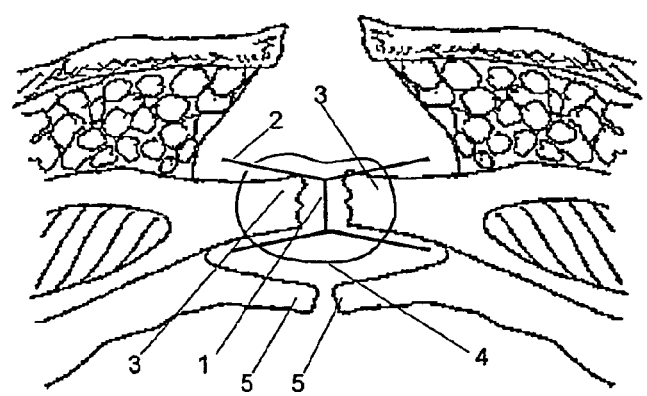
Fig.7

WALL PROSTHESIS THAT CAN BE IMPLANTED IN THE CENTER OF A WOUND TO REINFORCE ABDOMINAL WALL CLOSURE

RELATED APPLICATIONS

This application is a national stage filing under 35 U.S.C. §371 of International Application No. PCT/ES02/00384, filed Jul. 31, 2002, which is an international application of and claims priority to Spanish Application No. ES 2001/P01825, filed Aug. 3, 2001.

FIELD OF INVENTION

This invention is a prosthesis that can be implanted in surgical closures of the abdominal wall, characterized by tissue integration and stimulation of the connective tissue response in the center of wound scarring, increasing its resistance and thus preventing hernias from forming in the incision, to be used primarily in the field of abdominal surgery.

DISCUSSION OF RELATED ART

Surgical interventions in the abdominal cavity require an opening in the muscular aponeurotic surfaces covering the abdomen. This opening allows access to the unhealthy viscera, and is closed using suture wire upon completion of the operation. When the incision does not produce sufficient scar, an adverse effect occurs, which is the appearance of hernias in the region of the incision, hernias that cause esthetic deformity and compromise the herniated organs, and that can even be life-threatening, therefore necessitating a second intervention with all that that implies for the sole purpose of correcting the hernias. The frequency of surgical incision hernias of the abdomen is high, greater than 10% of interventions, particularly when the incision has been made at the midline, and can be higher in certain situations, making them by no means an insignificant problem.

The biologic cause of the hernias is a lack of stress resistance in the area of the scar. Once the sectioned aponeurotic planes have been closed using suture wire, proliferation of fibroblasts that segregate collagenous material, or scarring, should occur, which allows definitive resistance to be maintained. Under normal conditions, the resistance of an abdominal wall scar reaches only 70% of the original resistance at the end of one year. If some risk factor is added to this, such as advanced patient age, lung disease, obesity, kidney or liver disease, diabetes, use of certain medications, infections, etc., resistance is lower due to reduced collagen production, thereby favoring the frequent production of hernias.

Given the above facts, access to a system for somehow increasing the resistance of abdominal incision scars can be considered highly important for reducing undesirable complications from operations. In light of this, clinical work typically includes attempts to remove the above-mentioned risk factors, using suture wire with high biologic compatibility and permanence, and a careful suturing technique. However, all of these measures, which are currently routine, have failed to prove sufficient as evidenced by the above-mentioned hernia statistics. Finally, for years synthetic mesh made from plastic material that is used to strengthen and correct hernias has existed. This mesh is used on a large area, away from the center of aponeurotic scarring, and is not typically used with normal abdominal wall closures, mostly because placing it requires a special procedure that necessitates wide separation of flaps.

SUMMARY OF INVENTION

In order to increase the resistance of scars on the abdominal wall and reduce the likelihood of incisional hernias, a wall prosthesis that can be implanted in the center of a wound to reinforce abdominal wall closure has been designed, and is the subject of the present invention. In effect, the invention is tantamount to a new concept in wall prostheses that has not been used until now. This new prosthesis has been conceived for direct use at the center of connective scarring of the abdominal wall, in whose cavity is anchored the connective tissue of each side of the wound, in addition to stimulating formation of the same, which in turn increases the wound's resistance to traction, in terms of both time, as said resistance is achieved more quickly, and final results, as the final resistance achieved is superior.

To these ends, the proposed prosthesis is made from one or more flexible, biotolerated materials, such as a synthetic material, and includes two or more sheets or planes that are arranged at dihedral angles to each other. The sheets or planes are made in porous, tissue infiltratable, form, using interlaced or perforated fabric or any other method, and are provided with large pores that allow fibroblasts and collagenous fibers to proliferate, completely engulfing the prosthesis in their cavity. One of the sheets or planes is introduced between the edges of the connective tissue of the incision, such as the aponeurosis in an abdominal wall repair, into the center of scarring between the two connective surfaces to be joined, where it functions as a guide for placement and stimulation of connective tissue proliferation. The other plane(s) or sheet(s) of the prosthesis, overlap the connective edges, such as the aponeurotic edges of the section in an abdominal wall repair, either above the two sides, beneath them, or in both positions, where they are enclosed by the connective tissue, which they then stimulate as they proliferate. The resulting proliferation of tissue surrounding the prosthesis, in and around the center of scarring, allows the prosthesis to integrate with the surrounding tissue, and provides stress resistance greater than that obtained in standard closures performed with sutures without the use of the prosthesis, in terms of both final results and promptness of healing, greatly reducing the likelihood of hernia due to badly healed wounds.

Because of its novel placement at the center of scarring of the aponeurotic layer of the wound and the form in which it works, the wall prosthesis that can be implanted in the center of a wound to reinforce abdominal wall closure constitutes an advance in the state of the technique.

In one embodiment of the invention, a prosthesis may be provided for reducing the incidence of herniation at an incision or other opening in connective tissue, such as in an abdominal wall, through which access has been made to treat an anatomical area spaced from such connective tissue incision or other opening, the incision or other opening in the connective tissue having a length and a depth and defining first and second edges. The prosthesis may include a first biocompatible, implantable sheet that is integratable with the connective tissue. The first sheet having a length and a height. The length of the first sheet corresponding to a length of the incision or opening in the connective tissue, and the height of the first sheet corresponding to the depth of the incision or opening in the connective tissue. Also provided is a second biocompatible, implantable sheet that is integratable with the connective tissue. The second sheet having a length and a width. The length of the second sheet corresponding to a length of the incision or opening, and the width of the second sheet sufficient to overlap at least one of the first and second edges. The second sheet extends substantially transversely to the first sheet.

In another embodiment of the invention, a method is provided of reducing the incidence of herniation at an incision or other opening in connective tissue, such as in the abdominal wall, that is accessed to treat an anatomical area spaced from such connective tissue incision or other opening. The incision or other opening in the connective tissue defines a first edge and a second edge, and has a length and a depth. The method includes locating, in the incision or other opening in the connective tissue, a prophylactic, tissue integratable, prosthesis for reducing the incidence of herniation, and approximating together the first and second edges of the incision or other opening in the connective tissue.

BRIEF DESCRIPTION OF DRAWINGS

As an aid to understanding the invention's characteristics, a detailed description will be completed based on a set of plans that accompanies this descriptive report, in which the following has been laid out solely as a guide:

FIGS. 5 and 6 show a perspective view and cross section of another possible configuration of the invented prosthesis.

FIG. 7 shows a placement diagram of a model of the prosthesis at the center of scarring in the abdominal wall.

DETAILED DESCRIPTION

Figure 1:
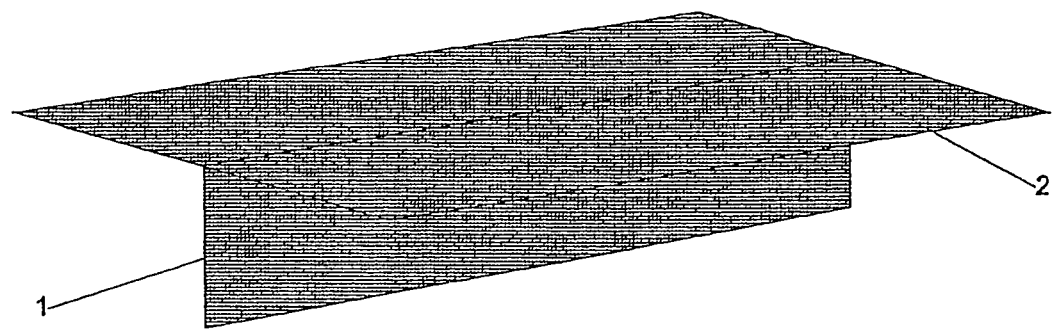
FIG. 1 is a perspective drawing of a general elevation of a prosthesis model derived from the current invention.
Figure 2:
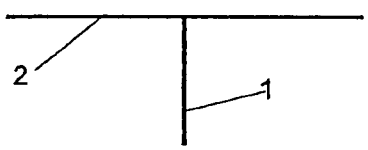
FIG. 2 shows a cross section of the model in FIG. 1.

Referring to these figures, the proposed prosthesis contains a sheet or plane of hernia resistant and flexible biotolerated material (1), preferably plastic, for example a type of polypropylene fabric in the form of an interlaced mesh with large pores. The sheet may be planar as shown. Examples of other biocompatible materials include, but are not limited to, polyamide, polyester, polyolefines and polytetrafluoroethylene. The material may be made up of fine threads with large pores, so that the connective tissue infiltrates between the pores. The plane or sheet (1) has a width that is proportional to the thickness of the aponeurosis to be joined, between whose sectioned ends it is placed, and length equal to that of the wound to be reinforced. Laid out substantially transversely to this plane or sheet, for example perpendicularly, is a second plane or sheet (2) that can exist singly as a T or V or can be double, taking the form of an H or X. This plane or sheet (2) is preferably made from the same material as the anterior plane or sheet and has sufficient width to form a single or double overlap covering the connective edges such as the aponeurotic edges in an abdominal wall repair, of each side of the wound to be joined, preferably with only a few millimeters of overlap per side, the length being the same as that of the wound. Any of the sides of the prosthesis may be cut during the surgical procedure to adapt to the concrete necessities of the wound being operated upon, without it being restricted to having any specific dimensions. With the prosthesis arranged in this manner, it is placed at the time of wound closure with plane or sheet (1) arranged vertically between the edges of the connective tissue (e.g., aponeurosis) (3) to be joined, leaving plane(s) or sheet(s) (2) arranged horizontally overlapping both sides of the connective tissue, such as the aponeurotic edges in an abdominal wall procedure. The prosthesis, once any of its sides has been cut to the size of the wound, is fixed in place by means of suturing (4), the technique that is currently used in the closure by approximation of connective tissue, such as the aponeurosis, and is covered in its lower portion by the peritoneum (5) in a way that prevents it from being exposed inside the abdominal cavity, thereby avoiding the formation of adhesions to abdominal viscera. As shown in FIG. 7, the connective tissue may be located beneath the dermis and subcutaneous fat. Once in position, the connective tissue is stimulated in and around the center of scarring of the sectioned aponeurosis, producing more acute scarring than that produced without the prosthesis, scarring that encloses the prosthesis and leaves it in place within the cavity of the newly formed collagen matrix. This produces initial stress resistance that is greater than that obtained with the simple closure used until now, which could remain greater over time, as suggested by animal experiments, than that of whole abdominal aponeurosis.

Figure 3:
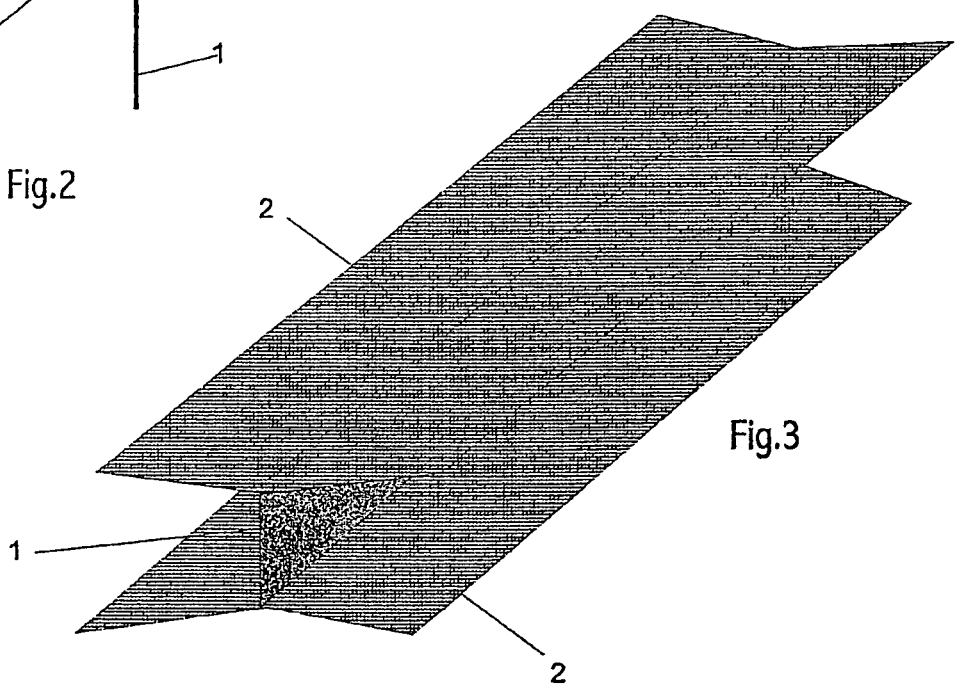
FIG. 3 shows a view of another possible prosthesis model derived from the current invention with a double overlap plan.
Figure 4:
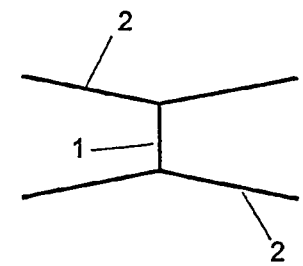
FIG. 4 shows a cross section of the model in FIG. 3.

The different sheets or planes that constitute the prosthesis can be manufactured to have a single structural and material form or may include scarring materials and configurations that differ from one another, as the situation warrants, it being possible to combine a lighter configuration with less material in one plane or sheet and more material in the other, or to make the prosthesis using material that is permanent or reabsorbed over time, either for all planes and sheets or only for some, without limits with regard to materials, dimensions, or geometric configuration of the sheets or planes. A sheet or plane may be made up of a single piece or several pieces joined in any manner, such as by fusion, heat, suturing or adhesion. As shown in FIG. 3, the sheet(s) or plane(s) for spanning the edges of connecting tissue may include diverging segments. In FIG. 5, the aspect of the prosthesis for spanning the edges of connecting tissue may include first and second segments that are spaced from one another, and the aspect of the prosthesis for location between the edges may include a pair of diverging segments.

What is claimed is:

1. A prosthesis for reducing the incidence of herniation in a patient who has not had a hernia at an incision or other opening in connective tissue through which access has been made to treat an anatomical area spaced from such connective tissue incision or other opening, the incision or other opening in the connective tissue having a length, a width and a depth, wherein the length and the depth define a first and a second edge, said prosthesis comprising:
   a first biocompatible, implantable sheet that is integratable with the connective tissue, said first sheet having a length and a height, said length of said first sheet corresponding to a length of the incision or opening in the connective tissue, and said height of said first sheet corresponding to the depth of the incision or opening in the connective tissue;
   a second biocompatible, implantable sheet that is integratable with the connective tissue, said second sheet having a length and a width, said length of said second sheet corresponding to a length of the incision or opening, and said width of said second sheet sufficient to overlap the width of the incision or other opening by a few millimeters per side;
   wherein said second sheet extends substantially perpendicularly to said first sheet;
   wherein the first and second sheets have large pores that allow fibroblasts and collagenous fibers to proliferate and completely engulf the prosthesis, and stimulate scarring.

2. The prosthesis of claim 1, wherein said first and second sheets are tissue infiltratable.

3. The prosthesis of claim 1, wherein said first and second sheets form a T-shape.

4. The prosthesis of claim 1, wherein said second sheet includes a first sheet segment and a second sheet segment that is spaced from the first sheet segment.

5. The prosthesis of claim 1, wherein said second sheet includes a pair of diverging sheets.

6. The prosthesis of claim 1, further including a third biocompatible, implantable sheet that is integratable with the connective tissue, said third sheet having a length and a width, said length of said third sheet corresponding to the length of the incision or opening, and said width of said third sheet sufficient to overlap the first and second edges, said third sheet extending substantially transversely to said first sheet.

7. The prosthesis of claim 6, wherein said third sheet is tissue infiltratable.

8. The prosthesis of claim 6, wherein said first, second and third sheets form an I-shape.

9. The prosthesis of claim 6, wherein said third sheet includes a pair of diverging sheets.

10. The prosthesis of claim 6, wherein said second sheet extends along a first end of said first sheet and said third sheet extends along a second end of said first sheet.

11. The prosthesis of claim 10, wherein said first end is opposite said second end.

12. The prosthesis of claim 6, wherein said third sheet is perpendicular to said first sheet.

13. The prosthesis of claim 6, wherein said second sheet and said third sheet are perpendicular to said first sheet.

14. The prosthesis of claim 1, wherein each of said first and second sheets is planar.

15. The prosthesis of claim 6, wherein each of said first, second and third sheets is planar.

16. The prosthesis of claim 1, wherein at least one of said first and second sheets is formed of resorbable material.

17. The prosthesis of claim 16, wherein both of said first and second sheets are formed of resorbable material.

18. The prosthesis of claim 6, wherein each of said first, second and third sheets is formed of resorbable material.

19. The prosthesis of claim 1, wherein said first and second sheets have substantially a same thickness.

20. The prosthesis of claim 6, wherein said first, second and third sheets have substantially a same thickness.

21. The prosthesis of claim 1, wherein said prosthesis, after implantation at the incision or other opening, stimulates greater formation of connective tissue at the incision or other opening than if the first and second edges were merely approximated together by suturing without inclusion of said prosthesis.

22. The prosthesis of claim 1, wherein the connective tissue is beneath dermis and subcutaneous fat.

23. The prosthesis of claim 1, wherein the connective tissue is located in an abdominal wall.

24. The prosthesis of claim 1, wherein the connective tissue is an aponeurosis.

25. The prosthesis of claim 1, wherein said second sheet is constructed and arranged to be positioned beneath the first and second edges of the incision or other opening in the connective tissue.

26. The prosthesis of claim 1, wherein said second sheet is constructed and arranged to be positioned above the first and second edges of the incision or other opening in the connective tissue.

27. A method of reducing the incidence of herniation in a patient who has not had a hernia at an incision or other opening in connective tissue that is accessed to treat an anatomical area spaced from such connective tissue incision or other opening, the incision or other opening in the connective tissue defining a first edge and a second edge, and the incision or other opening having a length, a width and a depth, said method comprising:
  positioning a prosthesis between the first and second edges of the incision or other opening in the patient who has not had a hernia, and
  suturing together the first and second edges of the incision or other opening, wherein at least one suture passes through the prosthesis,
  wherein the prosthesis comprises:
  a first biocompatible, implantable sheet that is integratable with the connective tissue, said first sheet having a length and a height, said length of said first sheet corresponding to the length of the incision or other opening, and said height of said first sheet corresponding to the depth of the incision or other opening, and
  a second biocompatible, implantable sheet that is integratable with the connective tissue, said second sheet having a length and a width, said length of said second sheet corresponding to the length of the incision or other opening, and said width of said second sheet sufficient to overlap the width of the incision or other opening by a few millimeters per side,
  wherein said second sheet extends substantially perpendicularly to said first sheet.

28. The method of claim 27, wherein the prosthesis is constructed and arranged to stimulate greater formation of connective tissue at the incision or other opening in the connective tissue than if the edges of the incision or other opening were merely approximated together by suturing without inclusion of the prosthesis.

29. The method of claim 27, wherein the prosthesis includes a tissue infiltratable material.

30. The method of claim 29, wherein the tissue infiltratable material is a sheet.

31. The method of claim 27, wherein the first and second sheets are tissue infiltratable.

32. The method of claim 27, wherein the first and second sheets form a T-shape.

33. The method of claim 27, wherein the second sheet of the prosthesis includes a pair of diverging sheets.

34. The method of claim 27, wherein the prosthesis further includes a third biocompatible, implantable sheet that is integratable with the connective tissue.

35. The method of claim 34, wherein the third sheet is tissue infiltratable.

36. The method of claim 34, wherein the third sheet of the prosthesis includes a pair of diverging sheets.

37. The method of claim 35, wherein the first, second and third sheets form an I-shape.

38. The method of claim 34, wherein the second sheet of the prosthesis extends along a first end of the first sheet of the prosthesis, and the third sheet of the prosthesis extends along a second end of the first sheet of the prosthesis.

39. The method of claim 34, wherein the third sheet of the prosthesis extends transversely to the first sheet of the prosthesis.

40. The method of claim 34, wherein each of the second sheet and the third sheet of the prosthesis extend transversely to the first sheet of the prosthesis.

41. The method of claim 27, wherein at least one of the first and second sheets is resorbable.

42. The method of claim 27, wherein both of the first and second sheets are resorbable.

43. The method of claim 34, wherein each of the first, second and third sheets are resorbable.

44. The method of claim 27, wherein the first and second sheets have substantially a same thickness.

45. The method of claim 34, wherein the first, second and third sheets have substantially a same thickness.

46. The method of claim 27, wherein each of the first and second sheets is planar.

47. The method of claim 34, wherein each of the first, second and third sheets is planar.

48. The method of claim 27, wherein the connective tissue is beneath dermis and subcutaneous fat.

49. The method of claim 27, wherein the connective tissue is located in an abdominal wall.

50. The method of claim 27, wherein there is a space between the first and second edges of the incision or other opening in the connective tissue prior to said positioning step, and wherein the width of the second sheet is sufficient to overlap the spaced apart first and second edges of the incision or other opening in the connective tissue.

51. The method of claim 34, wherein the third sheet has a length and a width, the length of the third sheet corresponding to the length of the incision or other opening in the connective tissue, and the width of the third sheet being sufficient to overlap the first and second edges of the incision or other opening in the connective tissue.

52. The method of claim 27, further including, before said positioning step, the step of treating, through the incision or opening, the anatomical area.

53. The method of claim 27, further comprising the step of selectively modifying the size or shape of the prosthesis to fit the incision or other opening in the connective tissue of the patient.

54. The method of claim 27, wherein the connective tissue is an aponeurosis.

55. The method of claim 34, wherein the second sheet overlaps a top or front surface of the first and second edges of the incision or other opening in the connective tissue, and the third sheet overlaps a bottom or rear surface of the first and second edges of the incision or other opening in the connective tissue.

56. The method of claim 27, wherein positioning the second sheet of the prosthesis includes positioning the second sheet of the prosthesis beneath the first and second edges of the incision or other opening in the connective tissue.

57. The method of claim 27, wherein positioning the second sheet of the prosthesis includes positioning the second sheet of the prosthesis above the first and second edges of the incision or other opening in the connective tissue.

58. The method of claim 27, wherein the first and second sheets have large pores that allow fibroblasts and collagenous fibers to proliferate and completely engulf the prosthesis, and stimulate scarring.

* * * * *